United States Patent [19]
Matsuda et al.

[11] Patent Number: 5,637,597
[45] Date of Patent: Jun. 10, 1997

[54] CARBOSTYRIL DERIVATIVES FOR INHIBITING PRODUCTION OF INTERLEUKIN-8

[75] Inventors: Takahide Matsuda, Kawasaki; Shigeru Owada, Musashino; Hiroshi Muta, Ashiya; Miki Aihara, Itano-gun; Hisao Takizawa, Itano-gun; Ken-ichi Imagawa, Itano-gun; Mikio Kikuchi, Kamakura, all of Japan

[73] Assignee: Otsuka Pharmaceutical Co., Ltd., Tokyo, Japan

[21] Appl. No.: 448,577

[22] PCT Filed: Oct. 17, 1994

[86] PCT No.: PCT/JP94/01739

§ 371 Date: Jun. 7, 1995

§ 102(e) Date: Jun. 7, 1995

[87] PCT Pub. No.: WO95/11026

PCT Pub. Date: Apr. 27, 1995

[30] Foreign Application Priority Data

| Oct. 21, 1993 | [JP] | Japan | 5-263417 |
| Oct. 21, 1993 | [JP] | Japan | 5-263418 |
| Oct. 21, 1993 | [JP] | Japan | 5-263419 |
| Apr. 27, 1994 | [JP] | Japan | 6-089641 |

[51] Int. Cl.$^6$ .................................. A61K 31/47
[52] U.S. Cl. .................................. 514/312
[58] Field of Search .................................. 514/312

[56] References Cited

FOREIGN PATENT DOCUMENTS

| 0147719 | 7/1985 | European Pat. Off. . |
| WO92/21342 | 10/1992 | WIPO . |
| WO93/00902 | 1/1993 | WIPO . |
| WO93/23043 | 11/1993 | WIPO . |
| WO94/12182 | 6/1994 | WIPO . |
| WO94/14444 | 7/1994 | WIPO . |
| WO94/20107 | 9/1994 | WIPO . |

OTHER PUBLICATIONS

Arzneimittel Forschung Drug Research 43 (I), No., 3, Mar. 1993, pp. 363–366.
Research Communications In Chemical Pathology and Pharmacology vol. 78, No. 3, pp. 259–277 (Dec. 1992).
Nippon Rinsho, vol. 51, No. 12, Dec. 1993, pp. 3154–3158.
Patent Abstracts of Japan vol. 15, No. 238 (C–841) [4766] (JP–A–3–74329), 1992.
Database WPI, Derwent Publication/Patent Abstracts of Japan, vol. 12, No. 365 (C–532) [3212] (JP–A–63–119467), 1988.
Patent Abstracts of Japan, vol. 14, No. 453 1990 (C–764) [4396] (JP–A–2–178227).

*Primary Examiner*—Marianne M. Cintins
*Assistant Examiner*—M. Moezie
*Attorney, Agent, or Firm*—Finnegan, Henderson, Farabow, Garrett & Dunner

[57] ABSTRACT

The present invention provides agents for inhibiting production of interleukin-8 and for inhibiting granulocytes activation as well as novel method for curing inflamatory diseases. The agents for inhibiting production of interleukin-8, and for inhibiting granulocytes activation and for curing inflammatory diseases, which contains as an active ingredient, a carbostyril derivative represented by the general formula (I):

$$\text{(I)} \quad \begin{array}{c} \text{CH}_2\text{CH}-\text{COOH} \\ | \\ \text{NHCO}-\text{Ar}-\text{R} \end{array}$$

(carbostyril ring with CH$_2$CH(NHCO-Ar-R)-COOH substituent)

where R is as described in the specification.

30 Claims, 2 Drawing Sheets

CARBOSTYRIL DERIVATIVES FOR INHIBITING PRODUCTION OF INTERLEUKIN-8

This application is a 371 of PCT/JP94/01739 filed Oct. 17, 1994.

FIELD OF THE INDUSTRIAL UTILIZATION

The present invention relates to an agent for inhibiting production of interleukin-8, an agent for inhibiting activation of granulocytes, an agent for curing inflammatory diseases, an agent for curing Behcet disease, an agent for curing stomatitis, an agent for curing nephritis and an agent for curing voice disorders. More particularly, the present invention relates to an agent for inhibiting production of interleukin-8, an agent for inhibiting activation of granulocytes, an agent for curing inflammatory diseases, an agent for curing Behcet disease, an agent for curing stomatitis, an agent for curing nephritis and an agent for curing voice disorders, all comprising, as an effective ingredient, a carbostyril derivative represented by the following general formula (I)

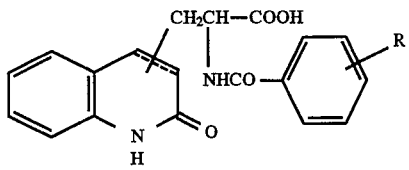

[wherein R is a halogen atom (a fluorine atom, a chlorine atom, a bromine atom or an iodine atom); the substitution site of the substituent on the carbostyril skeleton is 3- or 4-position of the carbostyril skeleton; and the carbon-carbon bond between 3- and 4positions in the carbostyril skeleton is a single bond or a double bond] or a salt thereof, preferably 2-(4-chlorobenzoylamino)-3-(2-quinolon-4-yl)propionic acid or a salt thereof.

BACKGROUND ART

The carbostyril derivatives represented by the above general formula (I) and the processes for producting thereof are described in Japanese Patent Publication No. 35623/1988. Further, the usefulness of the carbostyril derivative as an anti-gastric ulcer agent is described in Japanese Patent Application Kokai (Laid-Open) No. 74329/1991.

Also the usefulness of these carbostyril derivatives as an agent for curing diabetes is described in International Publication No. WO 92/21342; their usefulness as an agent for protecting intestinal mucosa from disorders is described in International Publication No. WO 94/12182; and their usefulness as an agent for inhibiting reduction in somatostatin secretion is described in International Publication No. WO 93/24043.

Interleukin-8 (hereinafter abbreviated to IL-8), which is also called a neutrophil leucocytes-activating factor, is a basic heparin binding polypeptide composed of 72 amino acids and is a cytokine produced not only from activated macrophages but also from various types of human cells.

IL-8 has various physiological activities such as the followings. (1) IL-8 is a chemotactic factor to neutrophil leucocytes, T cells and basophil leucocytes; (2) IL-8 activates neutrophil leucocytes, releases a lysosomal enzyme, changes the adhesion of neutrophil leucocytes to the endothelial cells of blood cells, and exasperates the inhibitory effect for propagation of candida species; (3) IL-8, when injected into joints, gives rise to destruction of synovial membrane accompanied with wetting of a large amount of neutrophil leucocytes; (4) IL-8 increases the appearance of adhesion factor on the surface of neutrophil leucocytes; (5) IL-8 controls the release of histamine from basophil leucocytes; and (6) IL-8 activates neutrophil leucocytes in artificial organs. IL-8 is also called as an inflammatory cytokine, and abnormal production of IL-8 and excessive reaction to IL-8 are thought to cause inflammatory diseases.

Behcet disease is a peculiar systemic inflammatory disease which attacks the mucous membrane of oral cavity, eyes, pudenda, skin and nearly all organs. The cause of the disease is said to be connected with infection, immunological abnormality, etc. but is not clarified yet. In curing the disease, there are used steroidal hormones, colchicine, Endoxan, cyclosporins, etc., but they must be used with the greatest possible care in view of their side effects. No useful curing agent has been found yet which is safe and can be administered over a long period.

The aphthous stomatitis caused by diseases such as stomatitis and the like is difficult to clinically distinguish from the aphthous stomatitis caused by Behcet disease and, similarly to Behcet disease, is intractable and recur often. In curing the disease, nosotropic therapies such as local administration of steroidal hormones, coating of silver nitrate, and the like are applied because the cause of stomatitis is unclear in many cases. In these therapies, however, continuous application is difficult because of, for example, the side effect of the substance used and, when the therapy is stopped, there is often seen recurrence of the disease. No useful curing agent has been found yet which is safe and can be administered over a long period. Stomatitis often shows an ulcerative symptom but there is no report mentioning that any anti-gastric ulcer agent is useful for such stomatitis.

Nephritis is thought to be caused not only by infection and an immunological mechanism but also by a nonimmunological mechanism. When nephritis is caused, for example, by various other diseases such as serum coagulation system disease, fibrinolytic system disease, hypertension and the like, it is said that nephritis is also induced by the quality of meal, etc. Thus, nephritis is a very complicated disease and is very difficult to cure. Hence, many researches are under way in order to find out an effective method for curing nephritis.

Curing of nephritis has hitherto been conducted by administering various drugs such as steroidal drug, immunosuppressive agent, non-steroidal anti-inflammatory agent, anticoagulant, antithrombocyte agent and the like. However, the steroidal drug shows a side effect when administered in a large amount over a long period; the immunosuppressive agent, showing a more striking side effect, must be used and applied with sufficient care; and the anticoagulant and the antithrombocyte agent are merely for alleviating the condition of nephritis and do not cure the root cause of the disease.

Hence, it is desired that the mechanism of nephritis development is clarified fully, that a reasonable method for curing nephritis is established and that a drug is developed which is effective for nephritis and which can be used safely over a long period.

In recent years, there has often been seen a case in which the excessive utterance required in special occupations owing to the change in social needs causes chorditis and consequent voice disorders. In such a case, since the excessive utterance is forced for occupational reasons, the voice disorders cannot be cured by silence cure, etc. when the patient is unable to fe freed from work. As a result, the vocal cord having inflammation is used excessively and it is often difficult to improve the voice disorders by an ordinary conservative cure alone. Hence, various researches are under way on a drug suitably used for cure of voice disorders. The methods currently used for curing voice disorders include spraying the throat with a vasoconstrictor or an adrenocortical hormone (this is a supplementary method), but the spraying method has a safety problem when continuously used over a long period. It is therefore desired to develop a drug which is low in side effect and which can be used safely over a long period.

DISCLOSURE OF THE INVENTION

The present inventors made extensive study in order to find a drug which is useful for the cure of inflammatory diseases because of its activity for cytokine as well as for activation and adhesivity of granulocytes and which can be used safely over a long period for the cure of Behcet disease, stomatitis, nephritis and voice disorders. As a result, the present inventors found out that the carbostyril derivatives represented by the above-mentioned general formula (I) or their salts, particularly 2-(4-chlorobenzoylamino)-3-(2-quinolon-4-yl)propionic acid or its salt has an excellent inhibitory activity for IL-8 production from IL-8 producing cells, an inhibitory activity for activation of granulocytes and an inhibitory activity for expression of adhesion factor of granulocytes; is effective for Behcet disease; is effective for the cure of painful- or painless-aphthous stomatitis which is caused by diseases such as stomatitis and the like and which gives the same symptom as Behcet disease; and is effective as an agent for curing deseases caused by increasing of the IL-8 production, an agent for curing deseases caused by the activation of granulocytes, an agent for curing deseases caused by increasing of the expression of adhesion factor of granulocytes, an agent for curing nephritis and an agent for curing voice disorders.

DETAILED DESCRIPTION OF THE PREFERRED EMBODIMENTS

Figure 1:
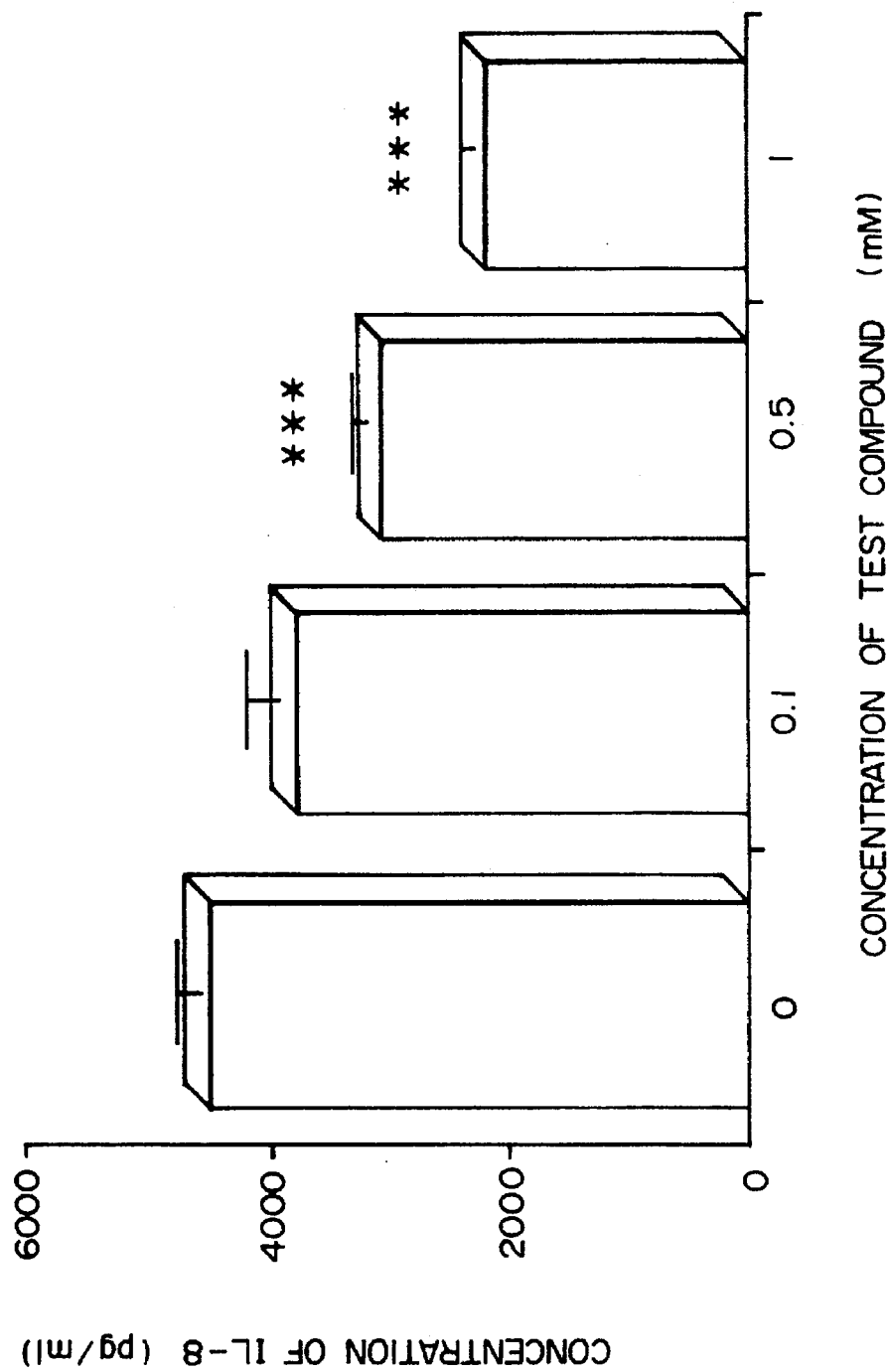
FIG. 1 is a graph showing the inhibitory activity of the present compound used as a test compound, i.e. 2-(4-chlorobenzoylamino)-3-(2-quinolon-4-yl)propionic acid for the acceleration of IL-8 production from IL-8 producing cells by *Helicobacter pylori* (hereinafter referred to as *H. pyroli*).

The agent for inhibiting interleukin-8 production, agent for inhibiting activation of granulocytes, agent for curing inflammatory diseases, agent for curing Behcet disease, agent for curing stomatitis, agent for curing nephritis and agent for curing voice disorders all according to the present invention, are obtained by converting a carbostyril derivative represented by general formula (I) or its salt into an ordinary pharmaceutical preparation.

Such a pharmaceutical preparation is prepared by using diluting agents or excipients ordinarily used, such as filler, bulking agent, binder, wetting agent, disintegrator, surfactant, lubricant and the like. The pharmaceutical preparation can be prepared in various forms depending upon the purpose of curing intended. Typical examples of the forms are tablets, pills, a powder, a solution, a suspension, an emulsion, granules, capsules, suppositories, an injection (e.g. solution or suspension) and an external preparation. It is also possible to use the compound of general formula (I) or its salt by mixing it with a resin or the like to increase its sustained releasability.

In preparing tablets, there can be used various carriers known in the art, exemplified by excipients such as lactose, white sugar, sodium chloride, glucose, urea, starch, calcium carbonate, kaolin, crystalline cellulose, silicic acid and the like; binders such as water, ethanol, propanol, simple syrup, lactose solution, starch solution, gelatin solution, carboxymethyl cellulose, shellac, methyl cellulose, potassium phosphate, polyvinylpyrrolidone and the like; disintegrators such as dry starch, sodium alginate, powdered agar, powdered laminarin, sodium hydrogen carbonate, calcium carbonate, polyoxyethylene sorbitan-fatty acid esters, sodium lauryl sulfate, stearic acid monoglyceride, starch, lactose and the like; disintegration inhibitors such as white sugar, stearin, cacao butter, hydrogenated oil and the like; absorption promoters such as quaternary ammonium salts, sodium lauryl sulfate and the like; humectants such as glycerine, starch and the like; adsorbents such as starch, lactose, kaolin, bentonite, colloidal silicic acid and the like; and lubricants such as refined talc, stearic acid salts, boric acid powder, polyethylene glycol and the like. The tablets can be prepared, as necessary, in the form of ordinary coated tablets, such as sugar-coated tablets, gelatin-coated tablets, enteric coated tablets or film-coated tablets, or in the form of double-layered tablets or multi-layered tablets.

In preparing pills, there can be used various carriers known in the art, exemplified by excipients such as glucose, lactose, starch, cacao butter, hardened vegetable oils, kaolin, talc and the like; binders such as powdered acacia, powdered tragacanth, gelatin, ethanol and the like; and disintegrators such as laminarin, agar and the like.

In preparing suppositories, there can be used carriers known in the art, exemplified by a polyethylene glycol, cacao butter, a higher alcohol, a higher alcohol ester, gelatin and a semi-synthetic glyceride.

In preparing an injection (solution, emulsion or suspension), it is generally sterilized and is preferably made isotonic to the blood. In preparing the solution, emulsion or suspension, there can be used all diluents commonly used in the art, such as water, ethyl alcohol, propylene glycol, ethoxylated isostearyl alcohol, polyoxyisostearyl alcohol and polyoxyethylene sorbitan-fatty acid esters. In this case, the injection may contain sodium chloride, glucose or glycerine in an amount sufficient to make the injection isotonic, and may further contain a solubilizing agent, a buffer solution, a soothing agent, etc. all ordinarily used. The injection may furthermore contain, as necessary, a coloring agent, a preservative, a perfume, a flavoring agent, a sweetening agent and other drugs.

The external preparation is prepared in the form of ordinary external preparation for pharmaceutical use. The ordinary external preparation for pharmaceutical use includes, for example, a solution, an oil, a lotion, a liniment, a fatty oil-based ointment, an emulsion type ointment (e.g., O/W type hydrophilic ointment or W/O type water-absorbing ointment), a water-soluble ointment, a paste, a plaster, a cream and an emulsion. The ordinary external preparation for pharmaceutical use is not restricted to the above Examples. Each of these forms can be prepared according to an ordinary method.

In shaping the external preparation, there can be used various materials known in the art. As the base, for example, there can be used at least one base selected from various oily bases or various water-soluble bases. Specific examples of the base are oils and fats such as peanut oil, sesame oil, soybean oil, safflower oil, avocado oil, sunflower oil, corn oil, rape seed oil, castor oil, camellia oil, coconut oil, olive oil, poppy seed oil, cacao oil, beef tallow, lard, wool fat and the like; modified oils and fats obtained by subjecting the above-mentioned oils and fats to chemical treatments (e.g. hydrogenation); mineral oils such as petrolatum, paraffin, silicone oil, squalane and the like; higher fatty acid esters, higher aliphatic alcohols and waxes such as isopropyl myristate, N-butyl myristate, isopropyl linoleate, propyl ricinoleate, isopropyl ricinoleate, isobutyl ricinoleate, heptyl ricinoleate, diethyl sebacate, diisopropyl adipate, cetyl alcohol, stearyl alcohol, bleached bees wax, spermaceti, Japan wax, hydrous lanolin, carnauba wax, shellac wax and the like; higher fatty acids such as stearic acid, oleic acid, palmitic acid and the like; mixtures of mono-, di- and tri-glycerides of saturated or unsaturated fatty acids of 12–18 carbon atoms; polyhydric alcohols such as ethylene glycol, polyethylene glycol, propylene glycol, polypropylene glycol, glycerin, Batyl Alcohol, pentaerythritol, sorbitol, mannitol and the like; gummy substances such as acacia, gum benzoin, guaiacum, tragacanth gum and the like; natural water-soluble polymers such as gelatin, starch, casein, dextrin, pectin, sodium pectate, sodium alginate, methyl cellulose, ethyl cellulose, carboxymethyl cellulose, hydroxyethyl cellulose, hydroxypropyl cellulose, nitrocellulose, crystalline cellulose and the like; synthetic water-soluble polymers such as polyvinyl alcohol, polyvinyl methyl ether, polyvinylpyrrolidone, sodium polyacrylate, carboxyvinyl polymer, polyethyleneimine and the like; nonionic, anionic or cationic or amphoteric surfactants; ethanol; isopropanol; and water. In the present invention, these bases can be used singly or in admixture of two or more.

The external preparation can contain, as necessary, additives of common use such as gelling agent, preservative, antioxidant, buffer, pH-controlling agent, wetting agent, antiseptic agent, coloring agent, aromatic agent, pigment, thickening agent, metal chelating agent and the like.

The aerosol type agent is prepared generally by preparing a sterilized solution or suspension containing the effective ingredient and then adding a propellant thereto. In preparing the solution or suspension, there can be used all diluents commonly used in the art, such as those mentioned with respect to the injection. As to the propellant, there can be used all propellants commonly used in the art, such as liquefied gas propellants for example, chlorofluorocarbons (e.g., Flon 12 or Flon 123), compressed gas propellants (e.g., nitrogen gas and carbon dioxide) and the like. The aerosol type agent may further contain a solubilizing agent, a buffer solution, etc., which are used commonly and, if necessary, the aerosol type agent may contain a coloring agent, a preservative, a perfume, a flavoring agent, a sweetening agent, etc.

The agent for inhibiting production of IL-8 of the present invention is useful for the prevention and cure of acute as well as chronic inflammatory diseases, based on the inhibitory activity for IL-8 production as well as on the inhibitory activity for activation of granulocytes. The agent is also useful for increasing the biocompatibilities of artificial organs and of artificial blood vessels. The inflammatory diseases include, for example, inflammatory dermal diseases such as inflammatory keratosis (e.g. psoriasis), atopic dermatitis, contact dermatitis and the like; chronic inflammatory diseases such as chronic rheumatoid arthritis, systemic lipus erythmatosus (SLE), Behcet disease and the like (these are autoimmune diseases); inflammatory intestinal diseases such as Crohn disease, ulcerative colitis and the like; inflammatory hepatic diseases such as hepatitis B, hepatitis C, alcoholic hepatitis, drug allergic hepatitis and the like; inflammatory renal diseases such as glumerulonephritis and the like; inflammatory respiratory system diseases such as bronchitis and the like; stomatitis; chorditis; and inflammations appearing during the use of artificial organs and artificial blood vessels. The inflammatory diseases to which the present agent is applicable, are not restricted only to the above mentioned examples.

The agent of the present invention inhibits (1) the acceleration of IL-8 production from IL-8 producing cells (e.g. peripheral blood monocyte, histiocytic macrophage, large granular lymphocyte, T lymphocyte, neutrophil leucocyte, fibroblast, endothelial cells of blood vessel, epidermal cell, liver cell, astral cell, bronchial epithelial cell and gastric carcinoma established cell line) by $H. pyroli$ which is said to have a connection with the appearance and recurrence of gastric mucosa injury, (2) the activation of neutrophil leucocytes and (3) the enhancement of adhesion factor. The present agent is therefore useful also for the prevention of appearance and recurrence of the gastric mucosa disorders caused by $H. pyroli$. Since $H. pyroli$ not only induces the activation of neutrophil leucocytes but also accelerates the appearance of ICAM-1 (ligand of LFA-1) in endothelial cells of blood vessel and cells of gastric mucosa, the present agent also has an inhibitory activity for the acceleration of appearance of ICAM-1 by $H. pyroli$.

The agent for curing Behcet disease and the agent for curing stomatitis both according to the present invention are used for the cure of various diseases of mucosa in oral cavity, eyes, pudenda, skin, etc., caused by Behcet disease. The agent can also be used for the cure of disorders of mucosa in oral cavity, caused by stomatitis, etc. The stomatitis includes, for example, catarrhal stomatitis, ulcerative stomatitis, aphthous stomatitis, herpetic stomatitis and toxic stomatitis.

The agent for curing nephritis according to the present invention is useful for acute, rapidly progressive or chronic nephritis which is thought to be caused by various reasons, and can be used for the cure of, in particular, chronic glomerulonephritis, etc. The acute nephritis includes, for example, glomerulonephritis or IgA glomerulonephritis after infection with hemolytic streptococcus, etc., chronic proliferative nephritis, crescent forming nephritis, lupus nephritis, necroticizing angitis and purpuric nephritis. The rapidly progressive nephritis includes, for example, crescent forming nephritis (extracanalicular proliferative glomerulonephritis). The chronic nephritis includes, for example, mesangial proliferative glomerulonephritis, membranous nephritis, membranous proliferative nephritis, focal glomerulonephritis, screlotic glomerulonephritis or purpuric angitis, and lupus nephritis.

The agent for curing voice disorders according to the present invention is useful for curing voice disorders which are thought to be caused by various reasons, and can be used for the cure of voice disorders of, in particular, people who make voices as a profession, such as singers, announcers and the like.

The amount of the carbostyril derivative (I) or its salt to be contained in the pharmaceutical preparation of the present invention is not particularly restricted and can be appropriately selected from a wide range, and the amount is generally 1–70% by weight, preferably 5–50% by weight in the pharmaceutical preparation.

The method for administering the pharmaceutical preparation is not particularly restricted. It is decided depending upon the form of preparation, the age, distinction of sex and other conditions of patient, the disease condition of patient, etc. For example, tablets, pills, a solution, a suspension, an emulsion, granules or capsules are administered orally. An injection is intravenously administered singly or in admixture with an ordinary auxiliary solution of glucose, amino acids or the like, or, as necessary, is singly administered intramuscularly, intradermally, subcutaneously or intraperitoneally. Suppositories are administered intrarectally. A solution, a suspension or a syrup type agent is orally administered. An aerosol type agent is administered directly onto the throat.

The dose of the present pharmaceutical preparation is appropriately selected depending upon the administration method, the age, distinction of sex and other conditions of patient, the disease condition of patient, etc., and the desirable dose is generally about 0.6–50 mg per kg of body weight per day in terms of the amount of the carbostyril derivative (1) or its salt. The desirable content of the effective ingredient in each unit of administration form is 10–1,000 mg.

EXAMPLES

The present agent is hereinafter described more specifically by showing Preparation Examples and Pharmacological Tests.

Preparation Example 1

| | |
|---|---|
| 2-(4-Chlorobenzoylamino)-3-(2-quinolon-4-yl)propionic acid | 150 g |
| Avicel (trade name for microcrystalline cellulose, product of Asahi Chemical Industry Co., Ltd. | 40 g |
| Corn starch | 30 g |
| Magnesium stearate | 2 g |
| Hydroxypropylmethyl cellulose | 10 g |
| Polyethylene glycol 6000 | 3 g |
| Castor oil | 40 g |
| Methanol | 40 g |

2-(4-Chlorobenzoylamino)-3-(2-quinolon-4-yl)propionic acid, Avicel, corn starch and magnesium stearate were mixed together and ground, then the mixture was made into tablets by using a tablet machine with a punch (R 10 mm). The tablets were coated with a film-coating agent consisting of hydroxypropylmethyl cellulose, polyethylene glycol 6000, castor oil and methanol, to produce film-coated tablets.

Preparation Example 2

| | |
|---|---|
| 2-(4-Chlorobenzoylamino)-3-(2-quinolon-4-yl)propionic acid | 150 g |
| Citric acid | 1.0 g |
| Lactose | 33.5 g |
| Dicalcium phosphate | 70.0 g |
| Prulonic F-68 | 30.0 g |
| Sodium lauryl sulfate | 15.0 g |
| Polyvinylpyrrolidone | 15.0 g |
| Polyethylene glycol (Carbowax 1500) | 4.5 g |
| Polyethylene glycol (Carbowax 6000) | 45.0 g |
| Corn starch | 30.0 g |
| Dry sodium lauryl sulfate | 3.0 g |
| Dry magnesium stearate | 3.0 g |
| Ethanol | A sufficient quantity |

2-(4-Chlorobenzoylamino)-3-(2-quinolon-4-yl)propionic acid, citric acid, lactose, dicalcium phosphate, Prulonic F-68 and sodium lauryl sulfate were mixed together.

The mixture was sieved through a No. 60 screen. The resulting sieved mixture was wet-granulated with an ethanol solution containing polyvinylpyrrolidone, Carbowax 1500 and Carbowax 6000. As necessary, ethanol was added to convert the mixture into a paste-like mass. Corn starch was added, and mixing was continued until uniform particles were formed. The resulting material was passed through a No. 10 screen, then placed in a tray, and dried in an oven of 100° C. for 12–14 hours. The dried particles were sieved through a No. 16 screen. To the resulting material were added dry sodium lauryl sulfate and dry magnesium stearate. The mixture was compressed into core tablets of desired shape with a tablet machine.

The core tablets were treated with a varnish and then sprayed with talc for prevention of moisture absorption. On the resulting core tablets was formed an undercoat layer. Sufficient times of varnish coating was conducted for internal use. Formation of undercoat layer and smooth coating were conducted to obtain completely round and smooth tablets. Color coating was conducted until a desired color was obtained. After drying, the coated tablets were polished to obtain tablets of uniform gloss.

Preparation Example 3

| | |
|---|---|
| 2-(4-Chlorobenzoylamino)-3-(2-quinolon-4-yl)propionic acid | 5 g |
| Polyethylene glycol (molecular weight: 4000) | 0.3 g |
| Sodium chloride | 0.9 g |
| Polyoxyethyiene sorbitan monooleate | 0.4 g |
| Sodium metabisulfite | 0.1 g |
| Methylparaben | 0.18 g |
| Propylparaben | 0.02 g |
| Distilled water for injection | 10.0 ml |

The parabens, sodium metabisulfite and sodium chloride were dissolved in the above distilled water of half the above volume at 80° C. with stirring. The solution was cooled to 40° C., and therein were dissolved 2-(4-chlorobenzoylamino)-3-(2-quinolon-4-yl)propionic acid, polyethylene glycol and polyoxyethylene sorbitan monooleate. To the solution was added the remaining distilled water to make a final volume. The solution was sterilized by passing through an appropriate filter paper, to prepare an injection.

Pharmacological Test 1

Inhibitory activity for production of IL-8

1) Cells used: Human gastric cancer strain MKN 45 incubated in RPMI 1640 culture medium containing 10% of heat inactivated FCS (fetal calf serum).

2) Stimulating substance for production of IL-8

Clinically isolated *H. pyroli* C0001 (obtained from Department of Internal Medicine, the Ohkura National Hospital).

The bacterium (*H. pyroli*) was incubated in a Brucella broth containing 7% of FCS and was used in an exponential growth phase.

3) Test compound 2-(4-Chlorobenzoylamino)-3-(2-quinolon-4-yl)propionic acid

4) Test method

A human gastric cancer cell line MKN 45 was inoculated on a 24-well culture plate in an amount of $0.3 \times 10^6$ cells/well. After the cells had adhered to the plate, the culture medium was changed to RPMI culture medium without antibiotic substance containing 10% of FCS. Thereto was added *H. pyroli* (clinical isolate C0001) in an amount of $1.2 \times 10^7$ cfu (cells:bacterium=1:400), after which incubation was conducted at a $CO_2$ concentration of 5% at 37° C. for 24 hours. The resulting mixture was subjected to centrifugation; the supernatant was recovered; and the amount of IL-8 in the supernatant was measured by EIA (enzyme immunoassay) according to a sandwich method [Microbiol. Immunol., vol. 36 (5), pp. 507–516, 1992].

5) Test Results

The test results are shown in FIG. 1. In FIG. 1, each data is shown as average ±SE, of four-time measurements, and each *** indicates p<0.001. As shown in FIG. 1, the test compound inhibited production of IL-8 from human gastric cancer MKN 45 cells, dependently upon the amount of the test compound used. Incidentally, the test compound showed no cytotoxicity when used in a concentration up to 5 mM.

Pharmacological Test 2

Effect on the activation of granulocytes

1) Cells used: Human neutrophil leucocytes isolated by the dextran Ficoll Paque sedimentation method.

2) Activating substance: *H. pyroli* cultured supernatant

*H. pyroli* (standard strain ATCC 43504) was incubated in Brucella broth containing 7% of heat inactivated FCS for 3 days. The resulting culture medium was subjected to centrifugation at 3,500 rpm for 10 minutes. The supernatant was filtered for sterilization.

3) Test compound 2-(4-Chlorobenzoylamino)-3-(2-quinolon-4-yl)propionic acid

This test compound was used by making into a 20 mM solution using NaOH and then diluting the solution with a culture medium for assay.

As to the antibody for surface antigen (CD11b), there was used FITC labelled CD11b (manufacture by Becton, Dickinson & Co.).

As to the culture medium for assay, there was used a RPMI culture medium containing 10% of FCS.

4) Test method

Human neutrophil leucocytes were inoculated on a 24-well culture plate in an amount of $5 \times 10^5$ cells/well. The wells were divided into a group (A) to which nothing was added (containing only neutrophil leucocytes), a group (B) to which *H. pylori* cultured supernatant (final concentration= 2%) was added, and a group (C) to which *H. pyroli* cultured supernatant (final concentration=2%) and the test compound (final concentration=10 µM, 50 µM, 100 µM or 500 µM) were added.

Each of 24-well culture plate was incubated in an incubator under an atmosphere containing 10% of $CO_2$, at 37° C. for 2 hours. After the incubation, the neutrophil leucocytes in each well were recovered, washed once with a FCM buffer solution (0.1% bovine serum albumin, 0.1% $NaN_3$/ phosphate-buffered saline), and then were reacted with the FITC labelled CD11b (antibody) on ice for 30 minutes. After the reaction, the reaction mixture was washed with the FCM buffer solution and analyzed by a flow cytometer. From the resulting histogram was calculated an average fluorescent intensity. By taking the appearance of CD11b in the non-stimulated neutrophil leucocytes (containing no *H. pyroli* cultured supernatant) as 100%, there was calculated the relative appearance of CD11b in each group.

5) Test results

Figure 2:
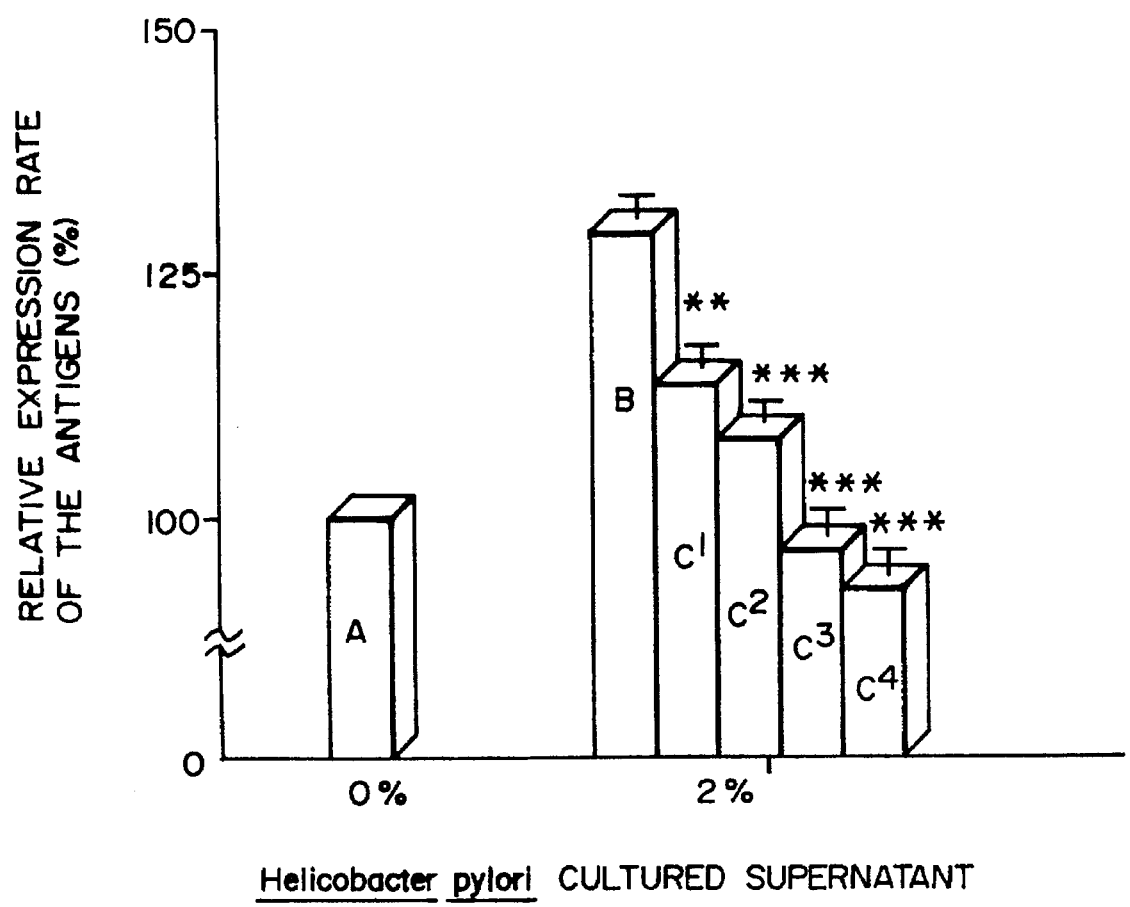
FIG. 2 is a graph showing the inhibitory activity of the present compound used as a test compound, i.e. 2-(4-chlorobenzoylamino)-3-(2-quinolon-4-yl)propionic acid for the activation of neutrophil leucocytes by *H. pyroli*.

The test results are shown in FIG. 2. In FIG. 2, each data is shown as average ±SE, of four-time measurements;  indicates p<0.01; and each * indicates p<0.001. Symbol A is the results of the group (A); B is the result of the group (B); and $C^1$, $C^2$, $C^3$ and $C^4$ are the results of the group (C) and are the results when the test compound was added at final concentrations of 10 µM, 50 µM, 100 µM and 500 µM, respectively. As shown in FIG. 2, the test compound inhibited the *H. pyroli*'s activity of augmentation of surface antigen, dependently upon the amount of the compound used.

Pharmacological Test 3

Test for examining the effect on stomatitis

1) Testees

There were tested eight patients of Behcet disease having aphthous ulcer in their oral cavities (age=18–45 years old, consisting of five males and three females).

2) Method of administration

In addition to the cure which had been conducted, 2-(4-chlorobenzoylamino)-3-(2-quinolon-4-yl)propionic acid was administered three times each day [one tablet each time (one tablet contained 100 mg of said compound)] for 6 months.

3) Method for evaluation

Each testee was requested to daily record "number of aphthous ulcers in oral cavity" and "degree of pain". They were each summed up monthly and their changes were calculated as follows.

$$\text{Change in number of aphthous ulcers in oral cavity (\%)} = \frac{1-(a)}{(b)} \times 100$$

(a): total number of aphthous ulcers during one month administration (b): total number of aphthous ulcers during one month before administration $$\text{Change in degree of pain (\%)} = \frac{1-(c)}{(d)} \times 100$$

(c): total point of degree of pain during one month administration (d): total point of degree of pain during one month before administration Incidentally, degree of pain was expressed as a point according to the following six-stage standard.

0: no pain

1: pain of no worry

2: not so strong pain

3: worrying pain

4: strong pain

5: very strong pain

Based on the changes (%), evaluation was made according to the following seven-stage standard.

Remarkable improvement: 60% or above

Improvement: 30% to below 60%

Slight improvement: 10% to below 30%

No change: below 10% to above −10%

Slight aggravation: −10% to above −30%

Aggravation: −30% to above −70%

Distinct aggravation: −70% or below

4) Results

With respect to the effect on the number of aphthous ulcers in oral cavity, four patients showed remarkable improvement; one patient showed improvement; two patients showed slight improvement; and one patient showed aggravation. With respect to the effect on pain, five patients showed remarkable improvement; one patient showed slight improvement; and two patients showed aggravation.

Pharmacological Test 4

Test for examining the effect on nephritis

1) Testees

Sixteen (16) persons who were confirmed by diagnosis to have chronic glomerulonephritis (age: 18–66 years old, consisting of ten males and six females).

2) Method of administration

Tablets each containing 100 mg of 2-(4-chlorobenzoylamino)-3-(2-quinolon-4-yl)propionic acid was orally administered three times each day (one tablet each time) for 12 weeks.

3) Method of evaluation

The urines which each testee discharged for 2–3 days before administration and for 2–3 days after administration of 12 weeks, were each accumulated. Each accumulated urine was measured for amount of urinary proteins. From each urinary protein amount obtained thus, its average amount per day was calculated. A decreasing value (%) in urinary protein amount was calculated from the following formula.

$$\text{Decreasing value in urinary proteins (\%)} = \frac{1-(e)}{(f)} \times 100$$

(e): daily average of urinary protein amount after administration;

(f): daily average of urinary protein amount before administration.

Based on the decreasing value in urinary protein (%), evaluation was made according to the following four-stage standard.

Improvement: 50% or above

Slight improvement: 25% or above to below 50%

No change: −25% or above to below 25%

Aggravation: below −25%

4) Test Results

Six persons showed improvement; two persons showed slight improvement; seven persons showed no change; and one person showed aggravation. Thus, half of the testees showed improvement or slight improvement.

Pharmacological Test 5

Test for examining the effect on voice disorders

1) Testees

Ten persons (singers, teachers, instructors of Chinese poem recitation, students of vocal music course in music academy, etc.) who were confirmed by diagnosis to have chorditis and consequent voice disorders as a result of excessive use of vocal cord for vocalization. Their ages ranged from 19 to 65 years old and they consisted of two males and eight females.

2) Method of administration

Tablets each containing 100 mg of 2-(4-chlorobenzoylamino)-3-(2-quinolon-4-yl)propionic acid was administered three times each day (one tablet each time). The administration was made continuously for 2–4 weeks until inflammation (when judged objectively) and voice disorders (when judged subjectively and objectively) came to show improvement.

3) Method of evaluation

The method for measuring the degree of voice disorders objectively by acoustic analysis, etc. is not established yet. Meanwhile, people who make voice for profession, are said to have rubefaction in the mucosa of vocal cord even in their normal conditions. In view of these matters, the effect of cure for voice disorders was evaluated based mainly on the degree of improvement in husky voice (judged subjectively) and the auditory examination made objectively, by referring to the objective observation of inflammation (e.g. rubefaction or swelling in mucosa of vocal cord) using an indirect larynx mirror, a stroboscope or the like.

The degree of husky voice was classified into the following four stages.

3: very strong

2: strong

1: slight

0: None

Using the above classification, the effect of cure for voice disorders was evaluated according to the following standard.

Remarkable effect: the degree of husky voice improved by three stages in four weeks.

Effect: the degree of husky voice improved by two stages in four weeks.

Slight effect: the degree of husky voice improved by one stage in four weeks.

No effect: No improvement in degree of husky voice

4) Results

Of the ten testees, three showed effect; three showed slight effect; and there was no testee who showed no effect. Further, there was no side effect which was considered to be due to the test compound used.

We claim:

1. Method for inhibiting production of interleukin-8, inhibiting expression of adhesion of granulocytes or inhibiting granulocytes activation, by administering a carbostyril derivative represented by the general formula (I):

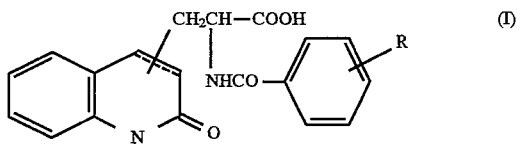

(wherein R is a halogen atom; the substitution site of side-chain of the formula:

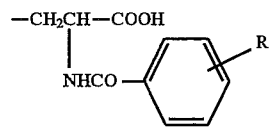

is 3- or 4-position in the carbostyril skeleton; and the carbon-carbon bond between 3- and 4-positions in the carbostyril skeleton is a single bond or a double bond), or salt thereof.

2. The method according to claim 1, wherein the carbostyril derivative represented by the general formula (I), or salt thereof is 2-(4-chlorobenzoylamino)-3-(2-quinolon-4-yl)propionic acid or pharmaceutically acceptable salt thereof.

3. Method for testing inflammatory dermal disease, autoimmune disease, inflammatory renal disease, inflammatory respiratory disease, stomatitis and chorditis, by administering a carbostyril derivative represented by the general formula (I):

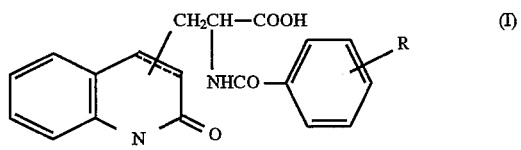

(wherein R is a halogen atom; the substitution site of side-chain of the formula:

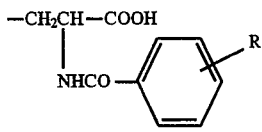

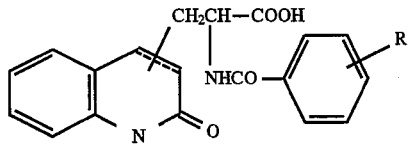

is 3- or 4-position in the carbostyril skeleton; and the carbon-carbon bond between 3- and 4-positions in the carbostyril skeleton is a single bond or a double bond), or salt thereof.

4. The method according to claim 3, wherein the carbostyril derivative represented by the general formula (I) or salt thereof is 2-(4-chlorobenzoylamino)-3-(2-quinolon-4-yl)propionic acid or pharmaceutically acceptable salt thereof.

5. The method according to claim 3, wherein the inflammatory dermal disease is an inflammatory keratosis (psoriasis).

6. The method according to claim 5, wherein the carbostyril derivative represented by the general formula (I) is 2-(4-chlorobenzoylamino)-3-(2-quinolon-4-yl)propionic acid or pharmaceutically acceptable salt thereof.

7. The method according to claim 3, wherein the inflammatory dermal disease is an atopic dermatitis.

8. The method according to claim 7, wherein the carbostyril derivative represented by the general formula (I) is 2-(4-chlorobenzoylamino)-3-(2-quinolon-4-yl)propionic acid or pharmaceutically acceptable salt thereof.

9. The method according to claim 3, wherein the inflammatory dermal disease is a contact dermatitis.

10. The method according to claim 9, wherein the carbostyril derivative represented by the general formula (I) is 2-(4-chlorobenzoylamino)-3-(2-quinolon-4-yl)propionic acid or pharmaceutically acceptable salt thereof.

11. The method according to claim 3, wherein the autoimmune disease is a chronic rheumatoid arthritis.

12. The method according to claim 11, wherein the carbostyril derivative represented by the general formula (I) is 2-(4-chlorobenzoylamino)-3-(2-quinolon-4-yl)propionic acid or pharmaceutically acceptable salt thereof.

13. The method according to claim 3, wherein the autoimmune disease is a systemic lupus erythematosus.

14. The method according to claim 13, wherein the carbostyril derivative represented by the general formula (I) is 2-(4-chlorobenzoylamino)-3-(2-guinolon-4-yl)propionic acid or pharmaceutically acceptable salt thereof.

15. The method according to claim 3, wherein the autoimmune disease is a Behcet disease.

16. The method according to claim 15, wherein the carbostyril derivative represented by the general formula (I) is 2-(4-chlorobenzoylamino)-3-(2-quinolon-4-yl)propionic acid or pharmaceutically acceptable salt thereof.

17. The method according to claim 3, wherein the inflammatory renal disease is a glomerulonephritis.

18. The method according to claim 17, wherein the carbostyril derivative represented by the general formula (I) is 2-(4-chlorobenzoylamino)-3-(2-quinolon-4-yl)propionic acid or pharmaceutically acceptable salt thereof.

19. The method according to claim 3, wherein the inflammatory respiratory disease is a bronchitis.

20. The method according to claim 19, wherein the carbostyril derivative represented by the general formula (I) is 2-(4-chlorobenzoylamino)-3-(2-quinolon-4-yl)propionic acid or pharmaceutically acceptable salt thereof.

21. Method for improving the bio-acceptability of an artificial organ or artificial blood vessel, by administering a carbostyril derivative represented by the general formula (I):

(wherein R is a halogen atom; the substitution site of side-chain of the formula:

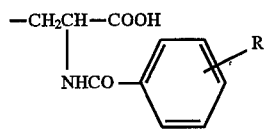

is 3- or 4-position in the carbostyril skeleton; and the carbon-carbon bond between 3- and 4-positions in the carbostyril skeleton is a single bond or a double bond), or salt thereof.

22. The method according to claim 21, wherein the carbostyril derivative represented by the general formula (I) or salt thereof is 2-(4-chlorobenzoylamino)-3-(2-quinolon-4-yl)propionic acid or pharmaceutically acceptable salt thereof.

23. Method for treating Behcet disease, by administering a carbostyril derivative represented by the general formula (I):

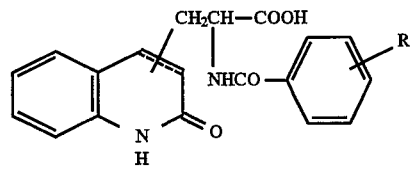

(wherein R is a halogen atom; the substitution site of side-chain of the formula:

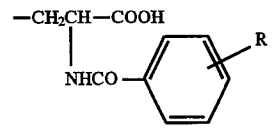

is 3- or 4-position in the carbostyril skeleton; and the carbon-carbon bond between 3- and 4-positions in the carbostyril skeleton is a single bond or a double bond), or salt thereof.

24. The method according to claim 23, wherein the carbostyril derivative represented by the general formula (I) is 2-(4-chlorobenzoylamino)-3-(2-quinolon-4-yl)propionic acid or pharmaceutically acceptable salt thereof.

25. Method for treating stomatitis by administering a carbostyril derivative represented by the general formula (I):

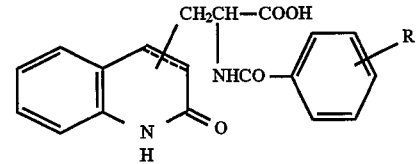

(wherein R is a halogen atom; the substitution site of side-chain of the formula:

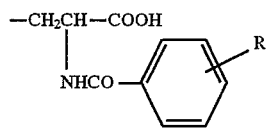

is 3- or 4-position in the carbostyril skeleton; and the carbon-carbon bond between 3- and 4-positions in the carbostyril skeleton is a single bond or a double bond), or salt thereof.

26. The method according to claim 25, wherein the carbostyril derivative represented by the general formula (I) is 2-(4-chlorobenzoylamino)-3-(2-quinolon-4-yl)propionic acid or pharmaceutically acceptable salt thereof.

27. Method for treating nephritis by administering a carbostyril derivative represented by the general formula (I):

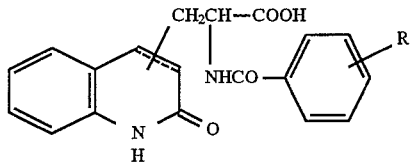

(wherein R is a halogen atom; the substitution site of side-chain of the formula:

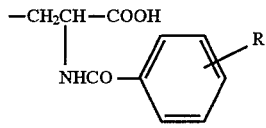

is 3- or 4-position in the carbostyril skeleton; and the carbon-carbon bond between 3- and 4-positions in the carbostyril skeleton is a single bond or a double bond), or salt thereof.

28. The method according to claim 27, wherein the carbostyril derivative represented by the general formula (I) is 2-(4-chlorobenzoylamino)-3-(2-quinolon-4-yl)propionic acid or pharmaceutically acceptable salt thereof.

29. Method for treating voice disorder by administering a carbostyril derivative represented by the general formula (I):

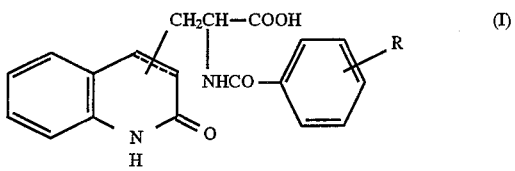

(wherein R is a halogen atom; the substitution site of side-chain of the formula:

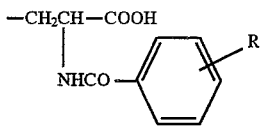

is 3- or 4-position in the carbostyril skeleton; and the carbon-carbon bond between 3- and 4-positions in the carbostyril skeleton is a single bond or a double bond), or salt thereof.

30. The method according to claim 29, wherein the carbostyril derivative represented by the general formula (I) is 2-(4-chlorobenzoylamino)-3-(2-quinolon-4-yl)propionic acid or pharmaceutically acceptable salt thereof.

* * * * *

UNITED STATES PATENT AND TRADEMARK OFFICE
CERTIFICATE OF CORRECTION

PATENT NO. : 5,637,597
DATED : June 10, 1997
INVENTOR(S) : Takahide Matsuda et al.

It is certified that error appears in the above-indentified patent and that said Letters Patent is hereby corrected as shown below:

Claim 3, column 12, line 54, "testing" should read --treating--.

Claim 14, column 13, line 45, "(2-guinolon-4-yl)" should read --(2-quinolon-4-yl)--.

Signed and Sealed this

Thirteenth Day of January, 1998

Attest:

BRUCE LEHMAN

Attesting Officer

Commissioner of Patents and Trademarks